United States Patent
Maubru et al.

(10) Patent No.: US 6,596,675 B2
(45) Date of Patent: Jul. 22, 2003

(54) WASHING COMPOSITION CONTAINING ALKYLAMIDO ETHER SULPHATES, ANIONIC SURFACTANTS AND CATIONIC POLYMERS

(75) Inventors: Mireille Maubru, Chatou (FR); Bernard Beauquey, Clichy (FR); Sandrine Decoster, Saint Gratien (FR)

(73) Assignee: L'Oreal, Paris (FR)

( * ) Notice: Subject to any disclaimer, the term of this patent is extended or adjusted under 35 U.S.C. 154(b) by 114 days.

(21) Appl. No.: 09/962,316

(22) Filed: Sep. 26, 2001

(65) Prior Publication Data

US 2002/0058596 A1 May 16, 2002

(30) Foreign Application Priority Data

Sep. 28, 2000 (FR) ............................................. 00 12377

(51) Int. Cl.$^7$ ........................... A61K 7/075; C11D 1/12; C11D 1/38; C11D 3/37
(52) U.S. Cl. ................ 510/123; 510/125; 510/426; 510/428; 510/433; 510/492; 510/504; 424/401; 424/70.5; 424/70.16; 424/70.19; 424/70.24; 424/70.28; 134/42
(58) Field of Search ................ 510/123, 125, 510/426, 428, 433, 492, 504; 424/401, 70.5, 70.16, 70.19, 70.24, 70.28; 134/42

(56) References Cited

U.S. PATENT DOCUMENTS

| | | | | |
|---|---|---|---|---|
| 6,417,145 | B1 | * 7/2002 | Decoster et al. | ............ 510/122 |
| 6,432,894 | B1 | * 8/2002 | Maurin et al. | ............... 510/122 |
| 6,506,372 | B1 | * 1/2003 | Dubief et al. | ............ 424/70.13 |
| 2002/0058596 | A1 | * 5/2002 | Maubru et al. | ............. 510/119 |

FOREIGN PATENT DOCUMENTS

| | | | |
|---|---|---|---|
| EP | 0 091 237 | 10/1983 | |
| EP | 0 761 205 | 1/1998 | |
| EP | 761205 | * 1/1998 | ............ A61K/7/50 |
| GB | 2 197 875 | 6/1988 | |

* cited by examiner

Primary Examiner—Mark Kopec
Assistant Examiner—Brian P. Mruk
(74) Attorney, Agent, or Firm—Steptoe & Johnson LLP; D. Douglas Price

(57) ABSTRACT

The present invention relates to a composition for washing keratin materials, comprising, in a cosmetically acceptable medium, at least one ($C_{8-30}$) alkylamido ether sulphate, at least one anionic surfactant chosen from ($C_6$–$C_{24}$)alkyl sulphates, ($C_6$–$C_{24}$) alkyl ether sulphates, ($C_6$14 $C_{24}$)alkyl ether carboxylates and anionic ($C_6$–$C_{24}$)alkyl polyglycosides, and at least one cationic polymer whose cationic charge density is greater than or equal to one milliequivalent per gram. The invention also relates to a cosmetic process for treating keratin materials using the composition according to the invention, and also to a use of this composition as a shampoo.

15 Claims, No Drawings

WASHING COMPOSITION CONTAINING ALKYLAMIDO ETHER SULPHATES, ANIONIC SURFACTANTS AND CATIONIC POLYMERS

The invention relates to a composition for washing keratin materials, comprising, in a cosmetically acceptable medium, at least one ($C_{8-30}$) alkylamido ether sulphate, at least one anionic surfactant and at least one cationic polymer, to a cosmetic process for treating keratin materials and to a use as a shampoo.

The known combinations of anionic surfactants and cationic polymers lead to cosmetic properties which are not entirely satisfactory, in particular on dried hair.

The Applicant has found, surprisingly, that the use of ($C_{8-30}$) alkylamido ether sulphate in combination with certain anionic surfactants and certain cationic polymers, in a cosmetically acceptable medium, improves the cosmetic properties of dried hair, in particular their smooth feel, manageability and sheen. In addition, this formulation has an excellent level of ocular tolerance, enabling it to be used in particular for children's shampoos.

One subject of the present invention is thus a composition for washing keratin materials, comprising, in a cosmetically acceptable medium, at least one ($C_{8-30}$) alkylamido ether sulphate, at least one anionic surfactant and at least one cationic polymer.

The expression "cosmetically acceptable medium" means a medium which is compatible with all keratin materials, such as the skin, the hair, the nails, the eyelashes and the eyebrows, the lips and any other area of the body and the face, and which also have a pleasant odour, appearance and feel.

Another subject of the invention consists of a cosmetic process for treating keratin materials using the abovementioned composition.

Another subject of the invention is a use of the composition according to the invention as a shampoo.

Other subjects, characteristics, aspects and advantages of the invention will emerge even more clearly on reading the description and the various examples which follow.

According to the invention, the washing composition comprises, in a cosmetically acceptable medium:
- at least one ($C_{8-30}$) alkylamido ether sulphate,
- at least one anionic surfactant chosen from ($C_6$–$C_{24}$) alkyl sulphates, ($C_6$–$C_{24}$) alkyl ether sulphates, ($C_6$–$C_{24}$) alkyl ether carboxylates and anionic ($C_6$–$C_{24}$) alkyl polyglycosides, and
- at least one cationic polymer whose cationic charge density is greater than or equal to 1 milliequivalent per gram (meq/g).

The ($C_{8-30}$) alkylamido ether sulphates which may be used in the composition according to the invention are in the form of salts of alkali metals such as sodium, of alkaline-earth metals such as magnesium, of ammonium or of amino alcohols.

The alkyl group containing from 8 to 30 carbon atoms and preferably from 10 to 20 carbon atoms may be linear or branched, and may be chosen in particular from lauryl, myristyl and palmityl groups.

The number of alkylene oxide units, preferably of ethylene oxide units, in the ($C_{8-30}$) alkylamido ether sulphates which is suitable in the invention is between 1 and 100 and preferably between 2 and 20.

Preferably, sodium lauryl/myristylamido ether sulphate containing 3 mol of ethylene oxide, sold under the name Laural® AMS by the company CECA, may be used in the composition according to the invention as ($C_8$–$C_{20}$) alkylamido ether sulphate.

The anionic surfactants which are suitable in the present invention are chosen from ($C_6$–$C_{24}$) alkyl sulphates, ($C_6$–$C_{24}$) alkyl ether sulphates, ($C_6$–$C_{24}$) alkyl ether carboxylates and anionic ($C_6$–$C_{24}$) alkyl polyglycosides that are well known in the art, and preferably from ($C_6$–$C_{24}$) alkyl ether sulphates.

They are in the form of salts of alkali metals, for example of sodium and of potassium, of alkaline-earth metals, for example of magnesium, of ammonium, or of amino alcohol. The anionic surfactants with ether units comprise a number of alkylene oxide units, preferably of ethylene oxide units, of between 1 and 100 and preferably between 2 and 20.

As examples of anionic alkyl polyglycosides, mention may be made in particular of alkylglycoside citrates and alkylglycoside tartrates, and as an example of ($C_6$–$C_{24}$) alkyl ether sulphate, mention may be made of sodium lauryl ether sulphate (70/30 C12/C14) containing 2.2 mol of ethylene oxide.

The washing composition according to the invention comprises one or more cationic polymers whose cationic charge density is greater than or equal to 1 milliequivalent per gram but preferably between 1 meq/g and 8 meq/g.

The cationic charge density may be determined according to the Kjeldahl method.

Cationic polymers with a cationic charge density of greater than or equal to 1 meq/g which may be used in accordance with the present invention may be chosen from all those that are already known per se as improving the cosmetic properties of hair treated with detergent compositions, namely, in particular, those described in patent application EP-A-0 337 354 and in French patent applications FR-A-2 270 846, 2 383 660, 2 598 611, 2 470 596 and 2 519 863.

Even more generally, in the context of the present invention, the expression <<cationic polymer>> denotes any polymer containing cationic groups and/or groups which may be ionized into cationic groups.

The cationic polymers are chosen from those which contain units comprising primary, secondary, tertiary and/or quaternary amine groups which may either form part of the main polymer chain or may be borne by a side substituent directly linked thereto.

The cationic polymers used generally have a number-average molecular mass of between 500 and $5 \times 10^6$ approximately and preferably between $10^3$ and $3 \times 10^6$ approximately.

Among the cationic polymers which may be mentioned more particularly are polymers of the polyamine, polyamino amide and polyquaternary ammonium type. These are known products.

The polymers of the polyamine, polyamido amide and polyquaternary ammonium type, which may be used in accordance with the present invention and which may be mentioned in particular, are those described in French patents Nos. 2 505 348 and 2 542 997. Among these polymers, mention may be made of:

(1) quaternized or non-quaternized vinylpyrrolidone/dialkylaminoalkyl (meth)acrylate copolymers, such as the products sold under the name "Gafquat®" by the company ISP, such as, for example, Gafquat® 734, 755 or HS100, or alternatively the product known as "Copolymére 937". These polymers are described in detail in French patents 2 077 143 and 2 393 573.

(2) Polymers consisting of piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2 162 025 and 2 280 361.

(3) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(4) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylaminohydroxypropyl/diethylenetriamine polymers sold under the name "Cartaretine F, F4 or F8" by the company Sandoz.

(5) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette® 101" by the company Hercules in the case of the adipic acid/epoxypropyl/diethylenetriamine copolymer.

(6) Cyclopolymers of methyldiallylamine or of dimethyldiallylammonium, such as the homopolymers or copolymers containing units corresponding to formulae (VI) or (VI'):

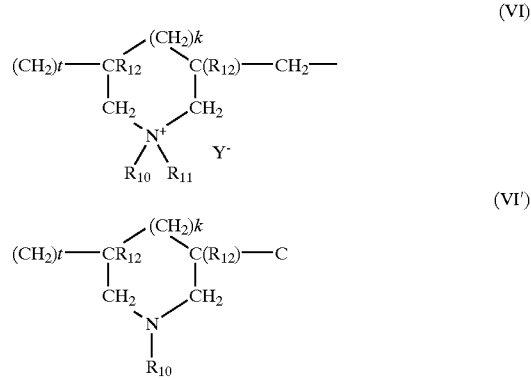

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group having from 1 to 22 carbon atoms, a hydroxyalkyl group in which the alkyl group preferably has 1 to 5 carbon atoms, or a lower amido-($C_1$–$C_4$) alkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described in particular in French patent 2 080 759 and in its Certificate of Addition 2 190 406.

Mention may be made, for example, of the diallyldimethylammonium chloride homopolymer sold under the name "Merquat® 100" by the company Calgon and the copolymers of diallyldimethylammonium chloride and of acrylamide sold under the name "Merquat® 550".

(7) The quaternary diammonium polymer containing repeating units corresponding to the formula:

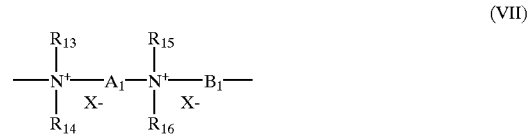

in which formula (VII):

$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$–$C_6$ alkyl radical substituted with a nitrile, ester, acyl or amide group or a group —CO—O—$R_{17}$—D or —CO—NH—$R_{17}$—D where $R_{17}$ is an alkylene radical and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and X⁻ denotes an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO—D—OC—$(CH_2)_n$— in which D denotes:

a) a glycol residue of formula: —O—Z—O—, where Z denotes a linear or branched hydrocarbon radical or a group corresponding to one of the following formulae:

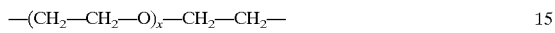

where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon radical, or alternatively the divalent radical

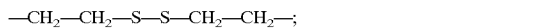

d) a ureylene group of formula: —NH—CO—NH—.

Preferably, X⁻ is an anion such as chloride or bromide.

These polymers generally have a number-average molecular mass of between 1000 and 100,000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use the polymers consisting of repeating units corresponding to the formula:

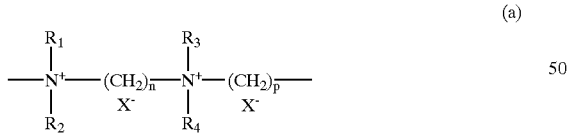

(a)

in which $R_1$, $R_2$, $R_3$ and $R_4$, which may be identical or different, denote an alkyl or hydroxyalkyl radical containing from 1 to 4 carbon atoms approximately, n and p are integers ranging from 2 to 20 approximately and X⁻ is an anion derived from an inorganic or organic acid.

One compound of formula (a) which is particularly preferred is the one for which $R_1$, $R_2$, $R_3$ and $R_4$ represent a methyl radical and n=3, p=6 and X=Cl, referred to as Hexadimethrine chloride according to the INCI (CTFA) nomenclature.

(8) Quaternary polyammonium polymers consisting of units of formula (VIII):

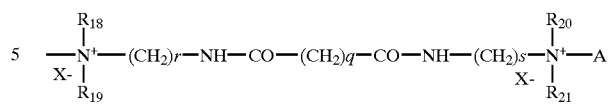

(VIII)

in which formula:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2(OCH_2CH_2)_p$OH radical, where p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, X denotes a halogen atom, A denotes a dihalide radical or preferably represents —$CH_2$—$CH_2$—O—$CH_2$—$CH_2$—.

Such compounds are described in particular in patent application EP-A-122 324.

Among these products, mention may be made, for example, of "Mirapol® A 15", "Mirapol® AD1", "Mirapol® AZ1" and "Mirapol® 175" sold by the company Miranol;

(9) homopolymers or copolymers derived from acrylic acid or methacrylic acid and comprising units:

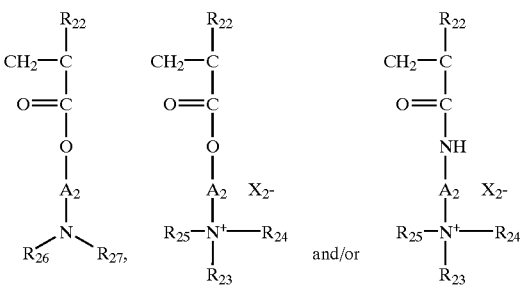

and/or in which the groups $R_{22}$ independently denote H or $CH_3$, the groups $A_2$ independently denote a linear or branched alkyl group of 1 to 6 carbon atoms or a hydroxyalkyl group of 1 to 4 carbon atoms, the groups $R_{23}$, $R_{24}$ and $R_{25}$, which may be identical or different, independently denote an alkyl group of 1 to 18 carbon atoms or a benzyl group, the groups $R_{26}$ and $R_{27}$ represent a hydrogen atom or an alkyl group of 1 to 6 carbon atoms, $X_2^-$ denotes an anion, for example methosulphate or halide such as chloride or bromide.

The comonomer(s) which may be used in the preparation of the corresponding copolymers belong(s) to the family of acrylamides, methacrylamides, diacetoneacrylamides, acrylamides and methacrylamides substituted on the nitrogen with lower alkyls, alkyl esters, acrylic acid or methacrylic acid, vinylpyrrolidone or vinyl esters.

(10) Quaternary polymers of vinylpyrrolidone and of vinylimidazole, such as, for example, the products sold under the names Luviquat® FC 905, FC 550 and FC 370 by the company BASF.

(11) Polyamines such as Polyquart® H sold by Henkel under the reference name "Polyethylene glycol (15) tallow polyamine" in the CTFA dictionary.

(12) Crosslinked polymers of methacryloyloxy ($C_1$–$C_4$) alkyltri ($C_1$–$C_4$) alkylammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is sold under the name "Salcaree® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which can be used in the context of the present invention, it is preferred to use cyclopolymers, in particular the polymers or copolymers of dimethyldiallylammonium chloride and of acrylamide, sold under the names "Merquat® 100" and "Merquat 550" by the company Calgon.

As other cationic polymers which are suitable in the present invention, mention may be made in particular of cellulose polymers, for example the cellulose ether derivatives comprising quaternary ammonium groups described in French patent No. 1 492 597, and in particular the polymers sold under the names "JR" (JR 400, JR 125 or JR 30M) or "LR" (LR 400 or LR 30M) by the company Union Carbide Corporation. These polymers are also defined in the CTFA dictionary as hydroxyethylcellulose quaternary ammoniums which have reacted with an epoxide substituted with a triethylammonium group.

Mention may also be made of cellulose copolymers or cellulose derivatives grafted with a water-soluble quaternary ammonium monomer, which are described in particular in U.S. Pat. No. 4 131 576, such as hydroxyalkylcelluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt.

The commercial products corresponding to this definition are more particularly the products sold under the name "Celquat® L 200" and "Celquat®H 100" by the company National Starch.

The washing composition according to the invention comprises the ($C_{8-30}$) alkylamido ether sulphates and anionic surfactants as mentioned above, in a total amount of between 3% and 50% by weight, and the cationic polymers in an amount of between 0.001% and 10% by weight and preferably between 0.05% and 5% by weight relative to the total weight of the composition.

The weight ratio between the anionic surfactants and the ($C_{8-30}$) alkylamido ether sulphates is preferably between 100 and 0.01 and preferentially between 20 and 1.

The cosmetically acceptable medium may consist of water or of a mixture of water and a cosmetically acceptable solvent such as a $C_1$–$C_4$ lower alcohol, for example ethanol, isopropanol, tert-butanol or n-butanol; alkylene glycols, for instance propylene glycol or glycol ethers; $C_5$–$C_{10}$ alkanes; acetone, methyl ethyl ketone; $C_1$–$C_4$ alkyl acetates, for instance methyl acetate, ethyl acetate or butyl acetate; dimethoxyethane or diethoxyethane; and mixtures thereof. The pH of the compositions of the invention is between 4 and 8 and preferably between 5 and 7.

The compositions according to the invention may also contain conventional additives that are well known in the art, such as natural or synthetic anionic, amphoteric, zwitterionic, nonionic or cationic, associative or non-associative polymeric thickeners, non-polymeric thickeners, for instance acids or electrolytes, nacreous agents, opacifiers, fragrances, mineral, plant and/or synthetic oils, esters of fatty acids or of polyethylene glycols, dyes, organic or mineral particles, volatile or non-volatile, modified or unmodified silicones, preserving agents and pH stabilizers.

A person skilled in the art will take care to select the optional additives and the amount thereof such that they do not harm the properties of the compositions of the present invention.

These additives are present in the composition according to the invention in an amount ranging from 0% to 20% by weight relative to the total weight of the composition.

The washing compositions according to the invention may be in the form of fluid or thickened liquids, gels, creams, mousses, simple emulsions or multiple emulsions.

They may be used, for example, as shampoos, rinse-out care products, deep-down care masks, shower gels or lotions or creams for treating the scalp.

The present invention also relates to a cosmetic process for treating keratin materials, which consists in applying an effective amount of a washing composition as described above to the keratin materials and in carrying out a rinsing operation, after an optional period of exposure.

According to one preferred embodiment of the invention, the composition may be used as a shampoo.

The example which follows illustrates the present invention and should not be considered in any way as limiting the invention.

EXAMPLE

A shampoo according to the invention was prepared using the following ingredients:

| | |
|---|---|
| Sodium lauryl ether sulphate (70/30 C12/C14) containing 2.2 mol of ethylene oxide | 7.0 g |
| Sodium lauryl/myristylamido ether sulphate (3 mol of ethylene oxide) as an aqueous 30% solution, sold by the company CECA under the name Laural ® AMS | 11.4 g |
| Mixture of oxyethylenated palm glycerides (200 mol of ethylene oxide) and of oxyethylenated coconut glyceride (7 mol of ethylene oxide) as an aqueous 70% suspension, sold by the company Goldschmidt under the name Antil ® 80 | 4.0 g |
| Oxyethylenated coconut mono/diglycerides (30 mol of ethylene oxide), sold by the company Goldschmidt under the name Rewoderm ® LI 63 | 4.0 g |

| | |
|---|---|
| Hydroxyethylcellulose crosslinked with epichlorohydrin and quaternized with trimethylamine, sold by the company Union Carbide under the name JR 400 | 0.25 g |
| Dioleate of polyethylene glycol (55 mol of ethylene oxide) and of propylene glycol, as an aqueous-alcoholic solution, sold by the company Goldschmidt under the name Antil ® 141 liquid | 2.0 g |
| Citric acid qs | pH 7 |
| Preserving agents | qs |
| Demineralized water qs | 100.0 g |

The shampoo according to the invention is applied to the hair and rinsed out, and the hair is dried.

The hair is observed to have a smooth feel and great manageability and sheen. This composition has good ocular tolerance.

What is claimed is:

1. A composition for washing a keratin material, comprising, in a cosmetically acceptable medium:
   (1) at least one ($C_{8-30}$)alkylamido ether sulphate,
   (2) at least one anionic surfactant, the at least one anionic surfactant being a ($C_6$–$C_{24}$)alkyl sulphate, a ($C_6$–$C_{24}$)alkyl ether sulphate, a ($C_6$–$C_{24}$)alkyl ether carboxylate or an anionic ($C_6$–$C_{24}$)alkyl polyglycoside, and
   (3) at least one cationic polymer having a cationic charge density greater than or equal to 1 milliequivalent per gram.

2. The composition according to claim 1, wherein the ($C_{8-30}$)alkylamido ether sulphate and the anionic surfactant are in the form of an alkali metal, alkaline-earth metal, ammonium or amino alcohol salt.

3. The composition according to claim 1, wherein the ($C_{8-30}$)alkylamido ether sulphate is sodium lauryl/myristylamido ether sulphate containing 3 mol of ethylene oxide.

4. The composition according to claim 1, wherein the anionic surfactant is a ($C_6$–$C_{24}$)alkyl ether sulphate.

5. The composition according to claim 1, wherein the ($C_{8-30}$)alkylamido ether sulphate and the anionic surfactant are present in a total amount of between 3% and 50% by weight relative to the total weight of the composition.

6. The composition according to claim 1, wherein the weight ratio between the anionic surfactant and the ($C_{8-30}$) alkylamido ether sulphate is between 100 and 0.01.

7. The composition according to claim 6, wherein the ratio between the anionic surfactant and the ($C_{8-30}$)alkylamido ether sulphate is between 20 and 1.

8. The composition according to claim 1, wherein the cationic polymer with a cationic charge density of greater than or equal to 1 milliequivalent per gram is:
   (1) a quaternized or non-quaternized vinylpyrrolidone/dialkylaminoalkyl (meth)acrylate copolymer;
   (2) a polymer consisting of a piperazinyl unit and a divalent alkylene or hydroxyalkylene radical containing a straight or branched chain, optionally interrupted by an oxygen, sulphur or nitrogen atom or by an aromatic or heterocyclic ring, or the oxidation or quaternization product of said polymer;
   (3) a water-soluble polyamino amide prepared by polycondensation of an acidic compound with a polyamine; said polyamino amide optionally crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative;
   the crosslinking agent being used in proportions ranging from 0.025 to 0.35 mol per amine group of the polyamino amide;
   said polyamino amide optionally being alkylated or, if it contains one or more tertiary amine functions, quaternized;
   (4) a polyamino amide derivative resulting from the condensation of a polyalkylene polyamine with a polycarboxylic acid followed by alkylation with a difunctional agent;
   (5) a polymer obtained by reaction of a polyalkylene polyamine containing two primary amine groups and at least one secondary amine group with a dicarboxylic acid which is a diglycolic acid or a saturated aliphatic dicarboxylic acid having from 3 to 8 carbon atoms;
   the molar ratio between the polyalkylene polyamine and the dicarboxylic acid being between 0.8:1 and 1.4:1; the polyamino amide resulting therefrom being reacted with epichlorohydrin in a molar ratio of epichlorohydrin relative to the secondary amine group of the polyamino amide of between 0.5:1 and 1.8:1;
   (6) a homopolymer or copolymer containing units corresponding to formulae (VI) or (VI'):

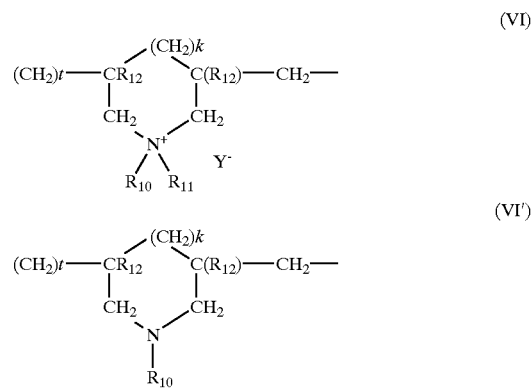

in which formulae k and t are equal to 0 or 1, the sum k+t being equal to 1;
$R_{12}$ denotes a hydrogen atom or a methyl radical;
$R_{10}$ and $R_{11}$, independently of each other, denote an alkyl group having from 1 to 22 carbon atoms, a hydroxyalkyl group in which the alkyl group has 1 to 5 carbon atoms, or a lower amido($C_1$–$C_4$)alkyl group, or $R_{10}$ and $R_{11}$ denote, together with the nitrogen atom to which they are attached, a heterocyclic group;
$Y^-$ is an anion which is bromide, chloride, acetate, borate, citrate, tartrate, bisulphate, bisulphite, sulphate or phosphate;
(7) a quaternary diammonium polymer containing repeating units corresponding to the formula:

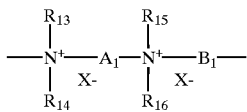 (VII)

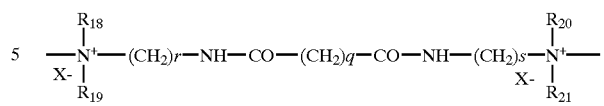 (VIII)

in which formula (VII):

$R_{13}$, $R_{14}$, $R_{15}$ and $R_{16}$, which may be identical or different, represent an aliphatic, alicyclic or arylaliphatic radical containing from 1 to 20 carbon atoms or a lower hydroxyalkylaliphatic radical, or alternatively $R_{13}$, $R_{14}$, $R_{15}$ and $R_{16}$, together or separately, constitute, with the nitrogen atoms to which they are attached, a heterocycle optionally containing a second heteroatom other than nitrogen, or alternatively $R_{13}$, $R_{14}$, $R_{15}$ and $R_{16}$ represent a linear or branched $C_1$–$C_6$ alkyl radical substituted with a nitrile, ester, acyl or amide group or a group —CO—O—$R_{17}$—D or —CO—NH—$R_{17}$—D where $R_{17}$ is an alkylene radical and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulphur atoms or a sulphoxide, sulphone, disulphide, amino, alkylamino, hydroxyl, quaternary ammonium, ureido, amide or ester group, and $X^{31}$ denotes an anion derived from an inorganic or organic acid;

$A_1$, $R_{13}$ and $R_{15}$ form, with the two nitrogen atoms to which they are attached, a piperazine ring; in addition, if $A_1$ denotes a linear or branched, saturated or unsaturated alkylene or hydroxyalkylene radical, $B_1$ denotes a group —$(CH_2)_n$—CO—D—OC—$(CH_2)_n$— in which D denotes:

a) a glycol residue of formula: —O—Z—O—, where Z denotes a linear or branched hydrocarbon radical or a group corresponding to one of the following formulae:

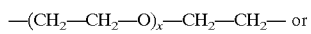

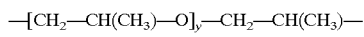

where x and y denote an integer from 1 to 4, representing a defined and unique degree of polymerization or any number from 1 to 4 representing an average degree of polymerization;

b) a bis-secondary diamine residue;

c) a bis-primary diamine residue of formula: —NH—Y—NH—, where Y denotes a linear or branched hydrocarbon radical, or alternatively the divalent radical

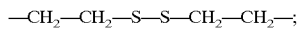

d) a ureylene group of formula: —NH—CO—NH—;

(8) a quaternary polyammonium polymer consisting of units of formula (VIII):

in which formula:

$R_{18}$, $R_{19}$, $R_{20}$ and $R_{21}$, which may be identical or different, represent a hydrogen atom or a methyl, ethyl, propyl, -hydroxyethyl, -hydroxypropyl or —$CH_2CH_2(OCH_2CH_2)_p$OH radical, where p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, X denotes a halogen atom, A denotes a dihalide radical or represents —$CH_2$—$CH_2$—O—$CH_2$—$CH_2$—;

(9) a homopolymer or copolymer derived from acrylic acid or methacrylic acid and comprising units:

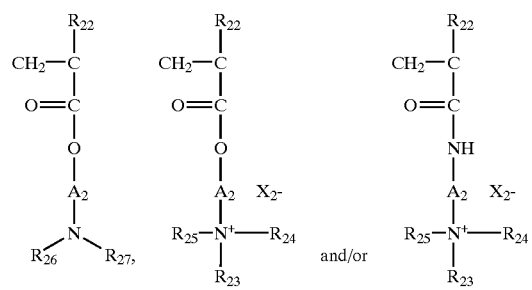

in which the groups $R_{22}$ independently denote H or $CH_3$, the group $A_2$ independently denotes a linear or branched alkyl group of 1 to 6 carbon atoms or a hydroxyalkyl group of 1 to 4 carbon atoms, the groups $R_{23}$, $R_{24}$ and $R_{25}$, which may be identical or different, independently denote an alkyl group of 1 to 18 carbon atoms or a benzyl group, the groups $R_{26}$ and $R_{27}$ represent a hydrogen atom or an alkyl group of 1 to 6 carbon atoms, $X_2^-$ denotes an anion;

(10) a quaternary polymer of vinylpyrrolidone and vinylimidazole;

(11) a crosslinked polymer of methacryloyloxy($C_1$–$C_4$)alkyltri($C_1$–$C_4$)alkylammonium salt;

(12) a polyalkyleneimine, a polymer containing a vinylpyridine or vinylpyridinium unit, a condensate of polyamine and of epichlorohydrin, a quaternary polyureylene or chitin derivative.

9. The composition according to claim 1, wherein the cationic polymer with a cationic charge density of greater than or equal to 1 milliequivalent per gram is a cellulose ether derivative comprising a quaternary ammonium group, a cellulose copolymer or a cellulose derivative grafted with a water-soluble quaternary ammonium monomer, or mixtures thereof.

10. The composition according to claim 1, wherein the cationic polymer is present in an amount of between 0.001% and 10% by weight relative to the total weight of the composition.

11. The composition according to claim 10, wherein the cationic polymer is present in an amount of between 0.05% and 5% by weight relative to the total weight of the composition.

12. The composition according to claim 1, wherein the cosmetically acceptable medium consists of water or a mixture of water and a cosmetically acceptable solvent.

13. The composition according to claim 1, wherein the composition further comprises a natural or synthetic anionic, amphoteric, zwitterionic, nonionic or cationic, associative or non-associative polymeric thickener, a non-polymeric thickener, a nacreous agent, an opacifier, a fragrance, a mineral, a plant or synthetic oil, an ester of a fatty acid or of a polyethylene glycol, a dye, an organic or mineral particle, a volatile or non-volatile, modified or unmodified silicone, a preserving agent or a pH stabilizer.

14. The composition according to claim 1, wherein the composition is a shampoo.

15. A cosmetic process for treating a keratin material, comprising applying a washing composition to the keratin material, the washing composition comprising, in a cosmetically acceptable medium:
 (1) at least one ($C_{8-30}$)alkylamido ether sulphate,
 (2) at least one anionic surfactant, the at least one anionic surfactant being a ($C_6$–$C_{24}$)alkyl sulphate, a ($C_6$–$C_{24}$) alkyl ether sulphate, a ($C_6$–$C_{24}$)alkyl ether carboxylate or an anionic ($C_6$–$C_{24}$)alkyl polyglycoside, and
 (3) at least one cationic polymer having a cationic charge density greater than or equal to 1 milliequivalent per gram.

* * * * *